United States Patent
Avantsa et al.

(10) Patent No.: US 8,765,476 B2
(45) Date of Patent: Jul. 1, 2014

(54) METHODS AND SYSTEMS FOR EFFICIENT AUTOMATIC SLIDE STAINING IN IMMUNOHISTOCHEMISTRY SAMPLE PROCESSING

(75) Inventors: Saradha Avantsa, Concord, CA (US); Ravishankar Melkote, Fremont, CA (US); Thomas Maxwell, Danville, CA (US); Geoffrey Cook, Santa Barbara, CA (US)

(73) Assignee: Biocare Medical, LLC, Concord, CA (US)

( * ) Notice: Subject to any disclaimer, the term of this patent is extended or adjusted under 35 U.S.C. 154(b) by 1052 days.

(21) Appl. No.: 12/645,340

(22) Filed: Dec. 22, 2009

(65) Prior Publication Data

US 2011/0151504 A1 Jun. 23, 2011

(51) Int. Cl.
*G01N 35/08* (2006.01)
*B01L 3/02* (2006.01)
*C12M 1/38* (2006.01)

(52) U.S. Cl.
USPC ............ 436/54; 435/7.1; 435/34; 435/40.51; 435/40.52; 435/286.7; 435/287.1; 435/287.6; 435/288.3; 436/43; 436/47; 436/51; 436/165; 436/166; 436/174; 436/176; 422/62; 422/63; 422/501; 422/504; 422/505; 422/508; 422/515; 422/519; 422/521; 422/522; 422/524; 422/532; 422/536; 422/560; 422/562; 422/563; 422/564

(58) Field of Classification Search
USPC ............ 435/7.1, 7.2, 34, 40.51, 40.52, 286.7, 435/287.1, 287.6, 288.3, 286.4; 436/43, 44, 436/46, 56, 164, 165, 166, 176, 47, 51, 54, 436/174; 422/63, 68.1, 73, 504, 505, 509, 422/524, 532, 536, 560, 562, 563, 564, 62, 422/501, 508, 515, 519, 521, 522
See application file for complete search history.

(56) References Cited

U.S. PATENT DOCUMENTS

| | | | |
|---|---|---|---|
| 4,341,736 A | | 7/1982 | Drbal et al. |
| 4,436,822 A | * | 3/1984 | Eseifan ..................... 436/164 |
| 4,635,791 A | | 1/1987 | Jackson et al. |
| 4,949,069 A | | 8/1990 | Wilson |
| 5,319,974 A | | 6/1994 | Lenz et al. |
| 5,654,199 A | | 8/1997 | Copeland et al. |
| 5,839,091 A | | 11/1998 | Rhett et al. |
| 6,093,574 A | | 7/2000 | Druyor-Sanchez et al. |
| 6,349,264 B1 | | 2/2002 | Rhett et al. |
| 6,495,106 B1 | | 12/2002 | Kalra et al. |
| 6,598,474 B2 | | 7/2003 | Purpura et al. |

(Continued)

OTHER PUBLICATIONS

Biocare Medical, LLC, intelliPATH Automated Slide Stainer Brochure, Oct. 21, 2007, 3 pages.*

*Primary Examiner* — Gail R Gabel
(74) *Attorney, Agent, or Firm* — Santangelo Law Offices, P.C.

(57) ABSTRACT

Automated sample processing systems may include onboard efficient high-speed mixing of at least two components with an automatic vertical force fluidic turbulent component mixer of which a mixed component may be aspirated and high-speed dispensed in a mixing vial. Other aspects may include single sweep applying a multi-treatment cleaning cycle to at least one slide. A multi-treatment cleaning cycle may include a washing treatment and a drying treatment. In yet other aspects the present invention may include an automated recovery sample processing system with the capability of detecting at least one immediate condition of a fortuitously terminated automatic sample processing run and perhaps even an automatic terminated sample processing run reconstruction calculator.

31 Claims, 9 Drawing Sheets

(56) References Cited

U.S. PATENT DOCUMENTS

| | | |
|---|---|---|
| 6,735,531 B2 | 5/2004 | Rhett et al. |
| 6,827,901 B2 | 12/2004 | Copeland et al. |
| 6,866,881 B2 | 3/2005 | Prentice et al. |
| 7,359,536 B2 | 4/2008 | Hays et al. |
| 7,400,983 B2 | 7/2008 | Feingold et al. |
| 7,410,753 B2 | 8/2008 | Hopkins et al. |
| 7,494,823 B2 | 2/2009 | Sukumar |
| 7,550,298 B2 | 6/2009 | Towne et al. |
| 7,553,672 B2 | 6/2009 | Bogen et al. |
| 7,584,019 B2 | 9/2009 | Feingold et al. |
| 7,593,787 B2 | 9/2009 | Feingold et al. |
| 2004/0033163 A1 | 2/2004 | Tseung et al. |
| 2004/0266015 A1* | 12/2004 | Favuzzi et al. ............ 436/48 |
| 2006/0134793 A1 | 6/2006 | Key et al. |
| 2006/0148063 A1 | 7/2006 | Fauzzi et al. |
| 2006/0153736 A1 | 7/2006 | Kalra et al. |
| 2006/0265133 A1 | 11/2006 | Cocks et al. |

* cited by examiner

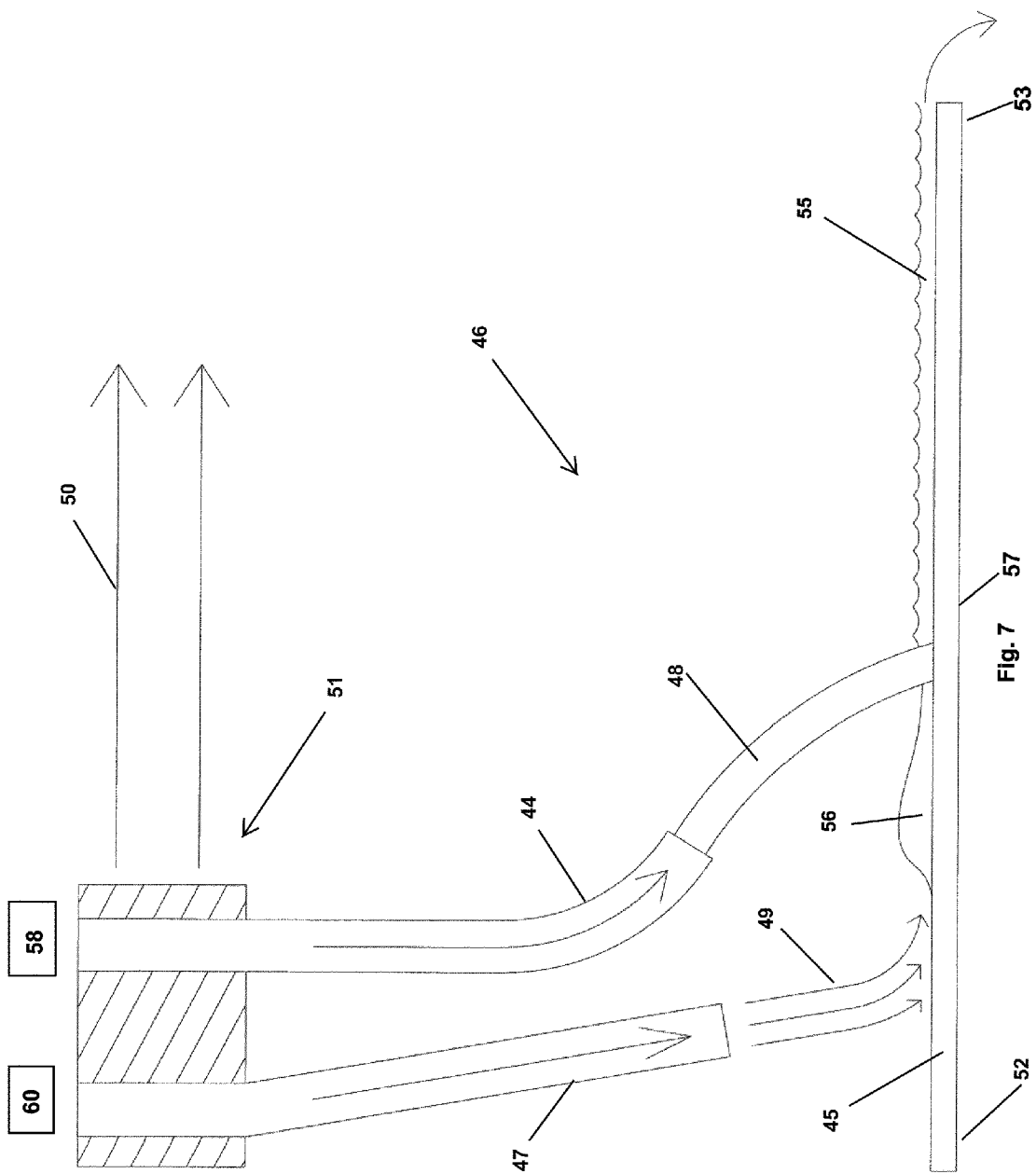

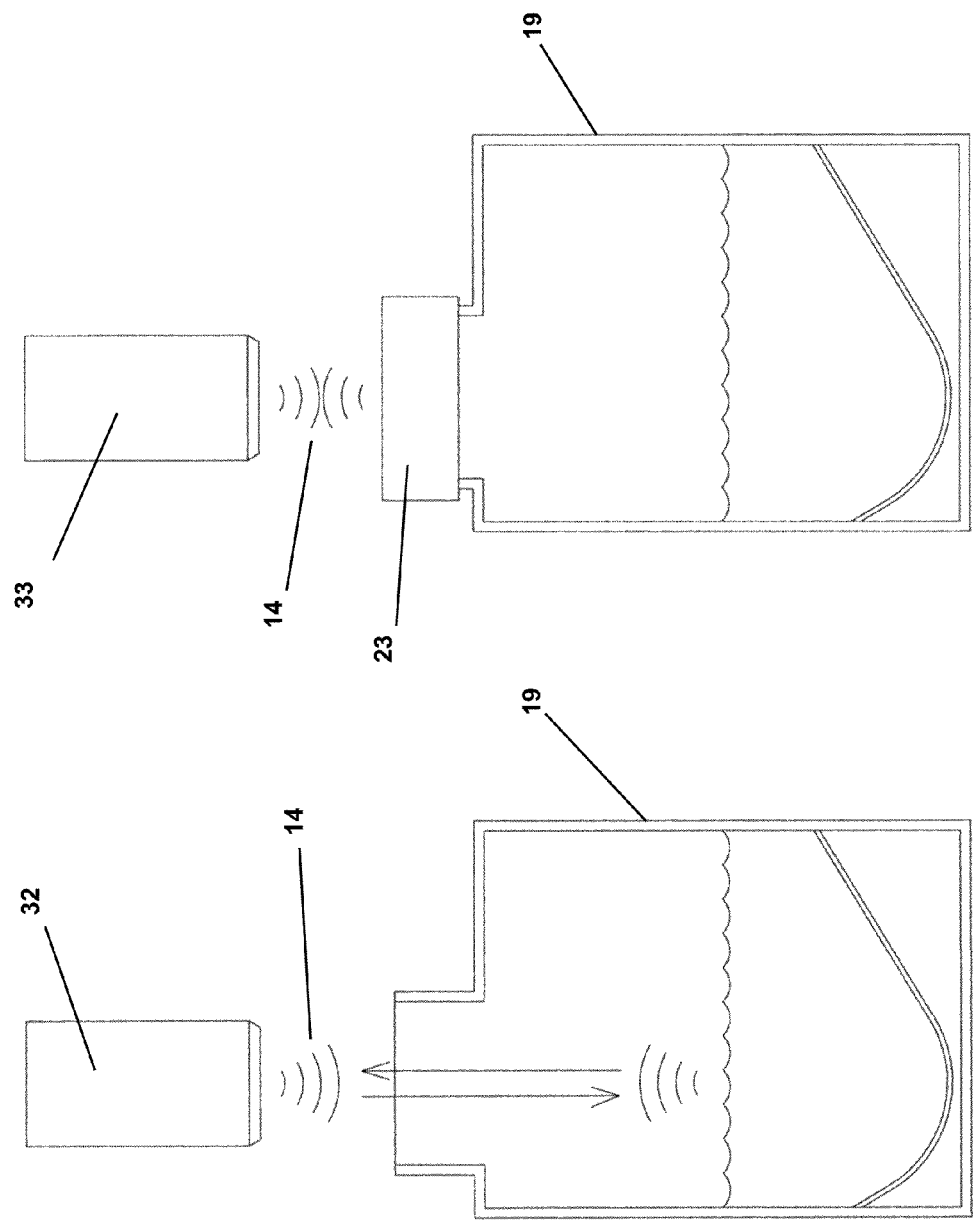

| intelliPATH | | | | |
|---|---|---|---|---|
| Slide | Protocol | Step | Time | Recover |
| A1 | ALKc | Block | 00:01:59 | ▸ |
| A2 | Bcl2 | Block | 00:02:00 | ▸ |
| A3 | CD10 | Block | 00:02:01 | ▸ |
| A4 | CD117 Ckit | Block | 00:02:03 | ▸ |
| A5 | CD15 Cocktail | Block | 00:02:17 | ▸ |
| A6 | CD20 | Block | 00:02:18 | ▸ |
| A7 | CD23 | Block | 00:02:19 | ▸ |
| A8 | CD3 | Block | 00:02:21 | ▸ |
| A9 | CD30 Ki1 | Block | 00:02:22 | ▸ |
| A10 | CD31 | Block | 00:02:23 | ▸ |
| B1 | CD34 | Block | 00:02:24 | ▸ |
| B2 | CD43 | Block | 00:02:25 | ▸ |
| B3 | CD68 KP1 | Block | 00:02:27 | ▸ |
| B4 | CD8 | Block | 00:02:04 | ▸ |
| B5 | CD99 | Block | 00:02:28 | ▸ |
| B6 | CDX2 | Block | 00:02:35 | ▸ |

Recover — 43

Cancel

Fig. 14

METHODS AND SYSTEMS FOR EFFICIENT AUTOMATIC SLIDE STAINING IN IMMUNOHISTOCHEMISTRY SAMPLE PROCESSING

BACKGROUND OF THE INVENTION

The present inventive technology, in embodiments, includes effective and efficient methods and systems relating to automatic slide staining in sample processing. Automatic slide stainer systems may be used to process a diversity of stains on various samples perhaps even simultaneously under computer control. Various staining procedures have been developed over the years to highlight various cellular or extracellular components of samples. Histochemical stains may employ chemical reactions to color various chemical moieties. Immunohistochemical stains may employ antibodies as probes to color specific proteins, perhaps through enzymatic deposition of a colored precipitate. The stains may therefore require the addition and removal of reagents in a defined sequence for specific time periods at perhaps even defined temperatures. Sample processing in immunohistochemical ("IHC") applications, for example and in other chemical and biological analyses may involve one or a number of various processing sequences or treatment protocols as part of an analysis of one or more samples.

In preparation for sample analysis, a biological sample may be acquired by known sample acquisition techniques and may comprise, for example in IHC applications, tissues generally or even in some applications one or a plurality of isolated cells, such as in microarray samples, and may be presented on a sample carrier including but not limited to microscope slides. Furthermore, the sample may be presented on the carrier variously and potentially in some form of preservation.

Even when performed automatically, there have been inefficiencies in past systems. Attempts have been made to automate sample processing to address the need for expedient sample processing. However, such previous efforts may not have fully addressed certain specific needs for an automated sample processing system. Shortcomings of conventional technologies relating to sample processing systems may include: the lack of a dependable system recovery, the lack of optimal reagent mixing in an automated process, the lack of efficient and effective slide cleaning, and perhaps even the lack of adequate detection of various aspects of an automation system.

Past efforts such as U.S. Pat. No. 4,341,736 to Drbal et al., U.S. Pat. No. 7,593,787 to Feingold, U.S. Pat. No. 7,400,983 to Feingold, U.S. Pat. No. 6,735,531 to Rhett, and U.S. Pat. No. 6,349,264 to Rhett, each hereby incorporated by reference herein, may not encompass the various advantages and other combinations of features as presented herein.

SUMMARY OF THE INVENTION

The present invention may provide an automated slide stainer using a suite of advanced technologies making it the intelligent choice for increased productivity and turn around time. It is an object of certain embodiments of the present invention technology to provide effective component combination in an automatic slide staining system such as for example in mixing stain components prior to application to a sample.

It is another object of certain embodiments of the present invention technology to provide an automated recovery system in the event of a failure to an automated stain sample processing system.

It is an object of certain embodiments of the present invention technology to provide efficient and perhaps even enhanced cleaning of a sample carrier such as a slide.

It is yet another object of certain embodiments of the present invention technology to provide detection of improper componentry installation such as for example missing or improperly installed vials, cap detection, and perhaps even reagent levels and the like.

Naturally, further objects, goals and embodiments of the inventions are disclosed throughout other areas of the specification and drawings.

BRIEF DESCRIPTION OF THE DRAWINGS

FIG. 7 shows an example of a single sweep multi-treatment cleaning applicator in accordance with various embodiments of the present invention.

FIG. 11 shows an example of an automatic dynamic component level detector detecting a component liquid level in a reagent vial in accordance with various embodiments of the present invention.

FIG. 12 shows an example of an automatic improper apparatus assembly detector detecting a cap on the reagent vial in accordance with various embodiments of the present invention.

FIG. 14 represents an example of an automated sample processing system in accordance with embodiments of the present invention.

DETAILED DESCRIPTION OF PREFERRED EMBODIMENTS

The present inventive technology includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

An automated sample processing system may be used to process biological samples on slides such as perhaps by staining and other processing techniques. An automated efficient sample processing system may provide a true continuous random access workflow with the efficiency of a high volume batch instrument. A system may enable running of simultaneous and independent batches that may prioritize in order of importance, perhaps ensuring that the runs are done on time, every time. Continuous random access may be provided so that it is not limited to "two batches per day". An operator may not have to wait for completion of the prior batch before more slides can be added or may not even have to wait until a certain number of samples come in to process an optimal batch size. In embodiments, an automated sample processing system may be capable of processing up to about five simultaneous runs or more perhaps by running individual trays independently with separate start and completion times and perhaps even by adding new batches of slides on-demand.

An automated sample processing system may be a fully open system, perhaps designed to use antibodies, detection systems or chromogens from any source and can provide maximum flexibility for both anatomic pathology and perhaps even research laboratories. It may be designed to run any test, at any time, with perhaps even any reagent. For example, an automated sample processing system may include an automated immunohistochemistry sample processing system which may provide methods of analyzing and identifying cell types based on the binding of antibodies to specific components of cells and tissues.

Figure 1:
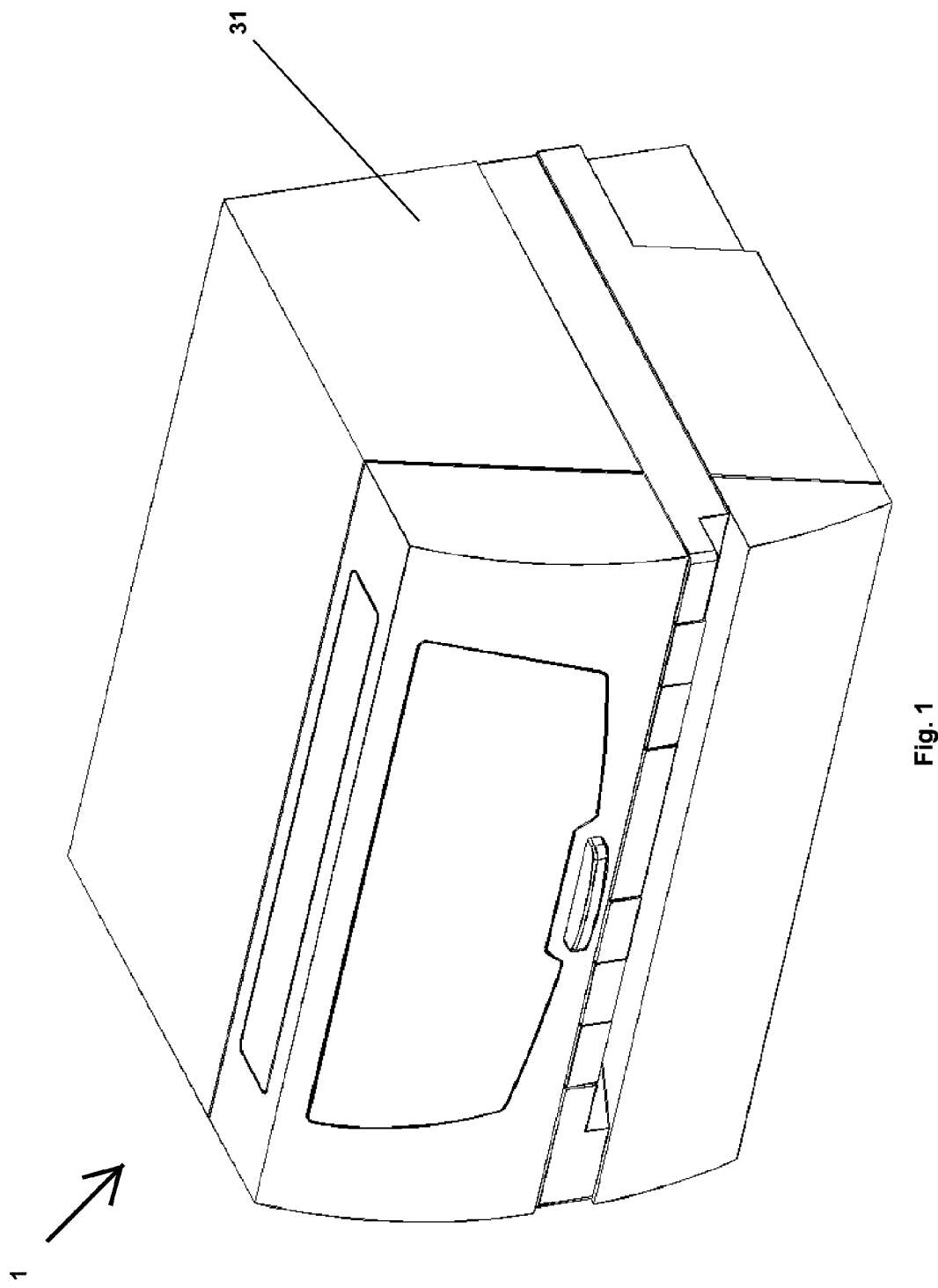
FIG. 1 shows one example of an automated sample processing system in accordance with various embodiments of the present invention.
Figure 2:
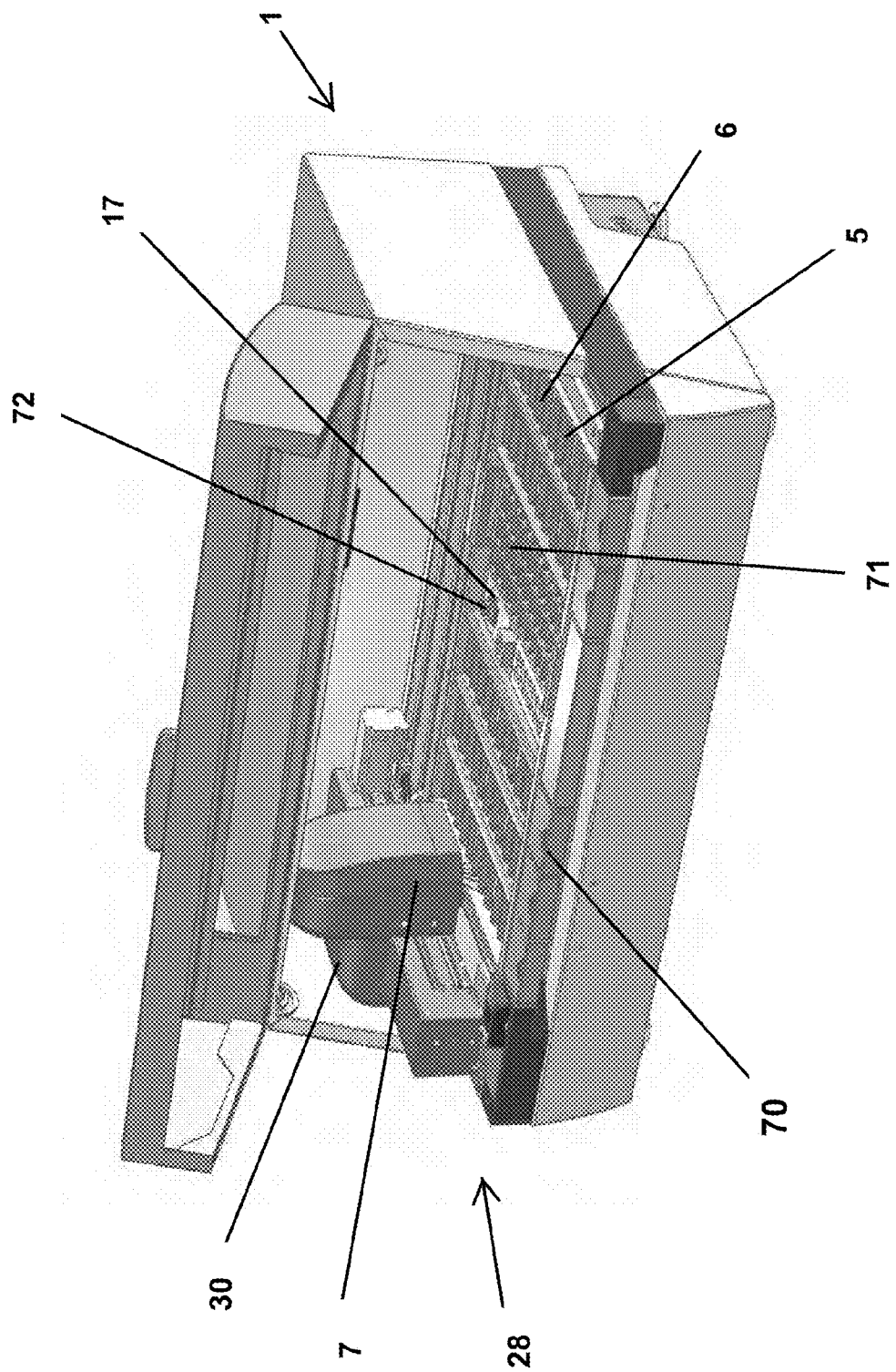
FIG. 2 shows an open housing of an automated sample processing system in accordance with various embodiments of the present invention.

In embodiments of the present invention, an automated sample processing system may feature methods and systems for effective reagent combination sample processing. For example, a system may provide preparation of chromogens and enzymes, such preparation may be perhaps onboard. Onboard mixing capabilities may provide speed and flexibility in an automated system. As can be understood from FIGS. 1 and 2, an automated sample processing system (1) may include an automated sample processing system housing (31), a robotic arm (7) responsive to a robotic motion system (28) which may process a plurality of biological samples (5) arranged on a plurality of slides (6) perhaps even located in at least one slide tray (70). The biological samples may be processed or perhaps even stained with components stored in the automated sample processing system housing (31). Components may be stored in reagent vials (71) that may be located in a cold station (17) of the system. The components may be transferred and mixed in at least one mixing vial (72) with the assistance of a robotic arm (7), aspirator and syringe pump, and a robotic motion system (28). The system may process up to about 50 slides or more and the biological samples may include any type of sample such as but not limited to a DNA sample, a RNA sample, a tissue sample, cell sample, blood sample, biopsy sample, and the like.

A cold station (17) may provide cold station mixing component storage which may include a refrigerated area on a deck perhaps holding up to two chromogen vials or more which may eliminate the need for the instrument to pause mid-run whilst the user comes back to apply unstable components such as but not limited to heat labile chromogens, Fast Red, and the like. This feature may enable a user to conveniently 'walk-away' or set up the system for overnight runs, thereby increasing the throughput and efficiency of laboratory processing. One purpose of a cold station may be to store unstable or perhaps even heat labile reagents. Unstable components may be a component that is unstable at room temperature and stable perhaps between about 2 to about 8° C. Unstable components may be kept at a cold temperature and an end product may be next right before use to ensure uniform and consistent staining for all the slides in the system. Without cold station and just-in-time mixing, it may not be possible to achieve consistent staining across all trays.

An automated sample processing system may be any type of system configured to automatically prepare components for application onto biological samples. In one embodiment, a method may include establishing an automated sample processing system, dispensing at least two components into a mixing vial, automatic vertically forced fluidic turbulent mixing of said at least two components in said mixing vial to create a uniform suspension of said at least two components, and perhaps even automatically applying at least a portion of said uniform suspension of said at least two components to a biological sample on a slide. Systems may include an automated sample processing system, a plurality of biological samples arranged on a plurality of slides located in said automated sample processing system, at least to mixing components, at least one mixing vial configured to contain at least a portion of said at least two mixing components in said automated sample processing system, an automatic vertical forced fluidic turbulent component mixer, and perhaps even an automatic uniform suspension slide applicator.

Figure 3:
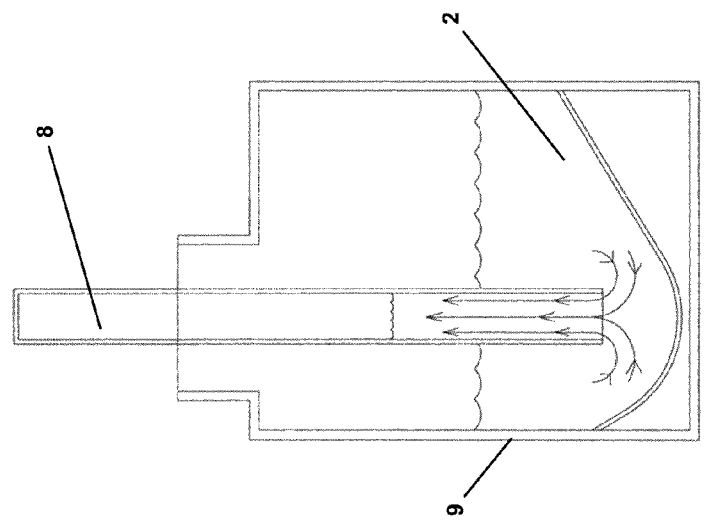
FIG. 3 shows an example of a probe aspirating liquid from a reagent vial of an automated sample processing system in accordance with various embodiments of the present invention.

In some embodiments, at least two components may need to be mixed prior to application onto a biological sample. As can be seen in FIG. 3, a probe (8) perhaps connected (either directly or indirectly) to a robotic arm (7) may move to at least one component source (9), may suction a mixing component (2) from the component source, and may place the mixing component (2) into a mixing vial (3). In embodiments, a component may be dispensed into a mixing vial near or perhaps at the base (13) of the vial perhaps with a base component dispenser to perhaps provide efficient dispensing and even mixing of the component. FIG. 3 shows movement of the mixing component as it is suctioned from the component source container into a probe (8). This may be repeated with at least one more component from at least one different component source to provide at least two components for mixture in a mixing vial. A mixing vial may be configured to contain at least a portion of at least two mixing components. For example, a mixing vial may provide a maximum liquid volume of up to about 6 milliliters. Of course, any volume may be used in other embodiments and all volumes are meant to be encompassed in this application.

In embodiments, a probe (8) may be a component transfer dispenser configured to take a portion of one of the components and place the portion into at least one mixing vial. A probe (8) may even be a mixing component suction element. A suction element or any suctioning steps may include any apparatus or method which may draw out or remove liquid from a source such as a container, vial, holder, or the like. For example, suctioning of a component may include aspirating a component from a component source with perhaps an aspirator or the like or even syringe pumping a component from a component source with perhaps a syringe pump or the like. The aspiration and dispense of components may be controlled by a syringe pump or aspirator or the like. An aspirator or syringe pump (30) may be located in a robotic arm of an automated sample processing system. Other embodiments could use other types of pumps to do the same operation. Of course, an automated sample processing system may provide any number of components including but not limited to at least two components, at least three components, at least four components, at least five components, at least six components, at least seven components, at least eight components, up to eight components, at least nine components, at least ten components or more, and the like.

A component of the present invention may include any type of biological sample processing substance including but not limited to reagents, chromogens, liquids, chemicals, enzymes, diluents, antibody diluents, blocking reagents, buffers, ancillary titration components, antibody titration components, any combinations thereof, and the like. A component may include a buffer, stabilizer, chromogen, hydrogen peroxide and the like and may be even be unstable or stable. Chromogens may include but are not limited to: Bajoran Purple Chromogen, Betazoid DAB Chromogen, DAB Chromogen, Cardassian Chromogen, Ferangi Blue Chromogen, Romulin AEC Chromogen, Vulcan Fast Red Chromogen, chromogens compatible with streptavidin horseradish peroxidase, chromogens for IHC staining, liquid stable DAB chromogen, and the like. Buffers may include but are not limited to DAB substrate buffer, Vulcan Buffer, and the like. Reagents may include but are not limited to blocking reagents, enzymes, antibody diluents, medical blocking reagents, endogenous peroxidase blockers, PEROXIDAZED 1, PeroxAbolish, background blockers, background eraser, background predator, background sniper, background terminator, mouse detective, blocking reagents for animal polymer detection (RUO), Rodent Block M—Blocking Reagent for Mouse Tissue, XM Factor, Rodent Block R—Blocking Reagent for Rat Tissue, XR Factor, medical enzymes, CAREZYME Series enzymes, CAREZYME I—Trypsin, CAREZYMEII—Pepsin, CAREZYME III—Pronase, Protease XXIV, intelliPATH FLX Pepsin, medical antibody diluents, increase titers, Protease and IgG-free, Reduce Background Staining, Ready-to-Use, Revival Series of Super Antibody Diluents, DaVinci Green, Monet Blue, Renoir Red, Van Gogh Yellow, VP Monet Blue, specialty antibody diluents, HPV Diluent, Renaissance, Biocare Medical Heat-Induced Epitope Retrieval Buffers, DECLOAKING Solutions buffers, Bull's Eye DECLOAKER, Antigen DECLOAKER, Nuclear DECLOAKER, EDTA DECLOAKER, Rodent DECLOAKER, PBS plus, TBS plus, Immunocare PBS, Immunocare TBS, Automation Wash Buffer, Tween 20, EcoMount, and the like. Accordingly, a system may be set up to mix at least two of the various components for the processing of biological samples on slides.

Figure 13:
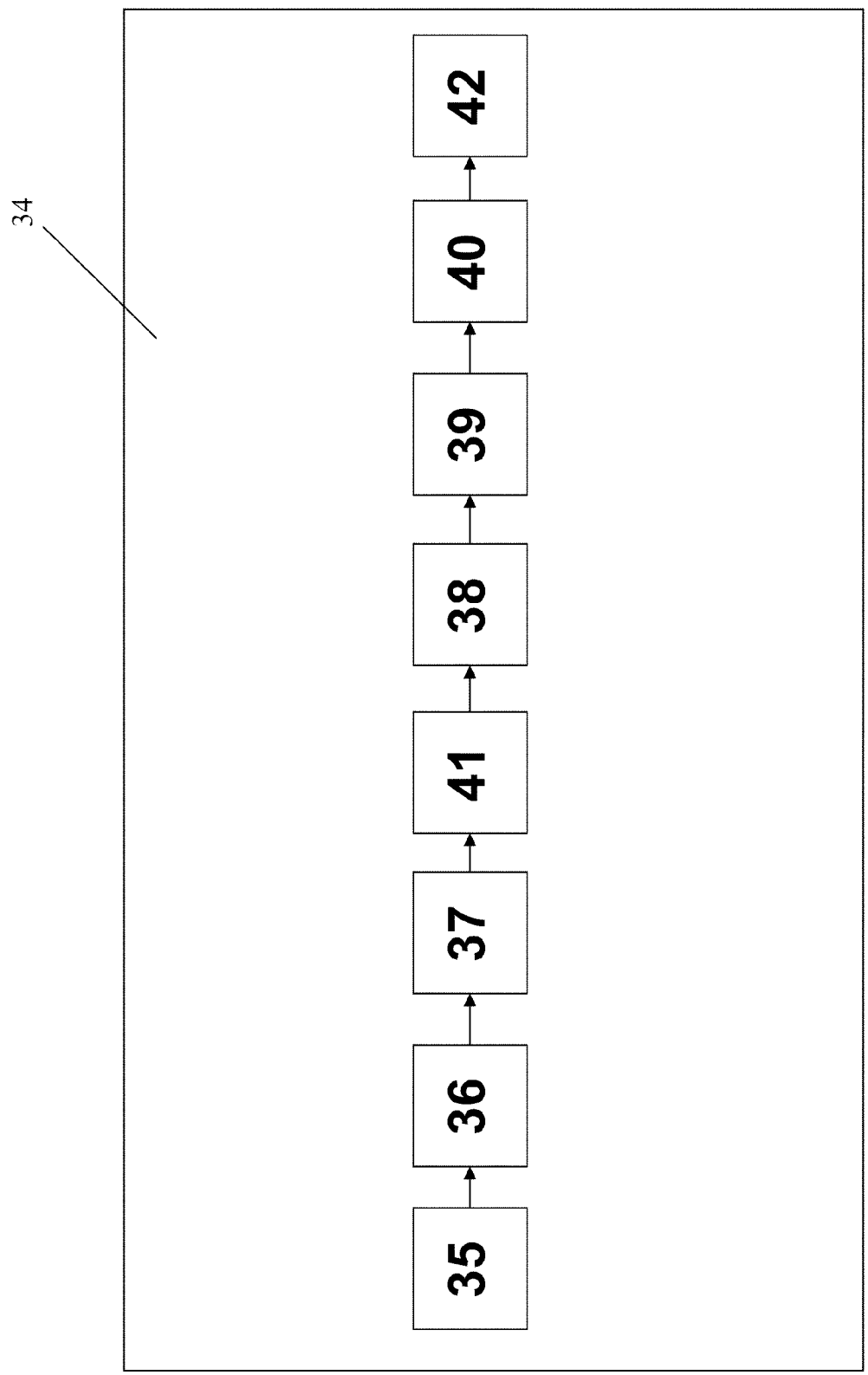
FIG. 13 is a schematic diagram of a generic embodiment of the invention.

As such, a dispensing of various components into mixing vials may be automatically dispensing of the components perhaps with an automated system. Embodiments may include a process operation control system which may be a computer software system to which the various apparatus parts respond. A process operation control system may automatically process the samples perhaps robotically with computer system. A sample processing system may be configured to achieve a sequence of events that achieves the desired result to some degree. In achieving this sequence in an automated fashion to some degree the sample processing system is deemed an automated sample processing system and achieves automatic processing of at least one sample. This automated sequence as well as other aspects of the invention may be controlled by hardware, software, or some combination of them to accomplish a desired sequence with limited human intervention. Regardless how achieved, the automated control may be provided by a process operation control system to direct the various activities. As shown in FIG. 13, this (as well as other functionalities discussed) may be software programming or subroutines; again it may also include hardware or the like. As mentioned above, a robotic motion system may be responsive to a process operation control system of an automated sample processing system. A robotic motion system (28) may include a robotic arm (7) connected (either directly or indirectly) to perhaps a probe (8). A robotic arm may provide simultaneous x-y motion to decrease the dispense time by perhaps about 10-20% resulting in faster turn around time. A robotic arm may allow a Z axis range of motion (20) of a probe into various vials.

Figure 5:
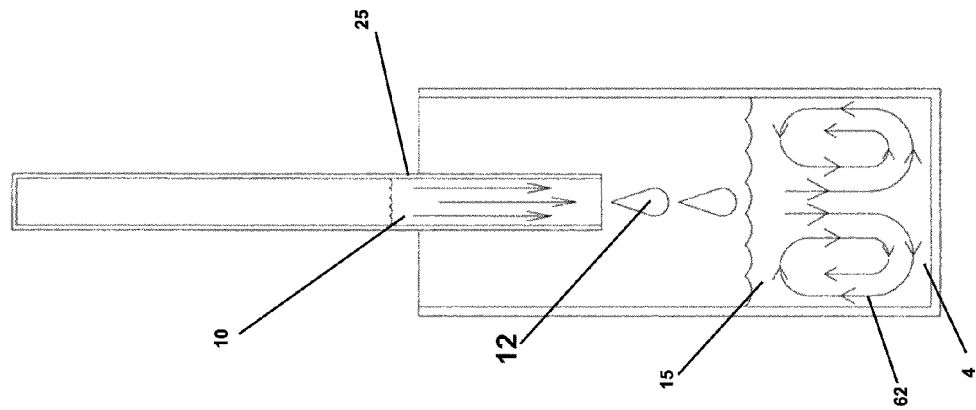
FIG. 5 shows an example of high-speed dispensing a mixed component of an automated sample processing system in accordance with various embodiments of the present invention.
Figure 4:
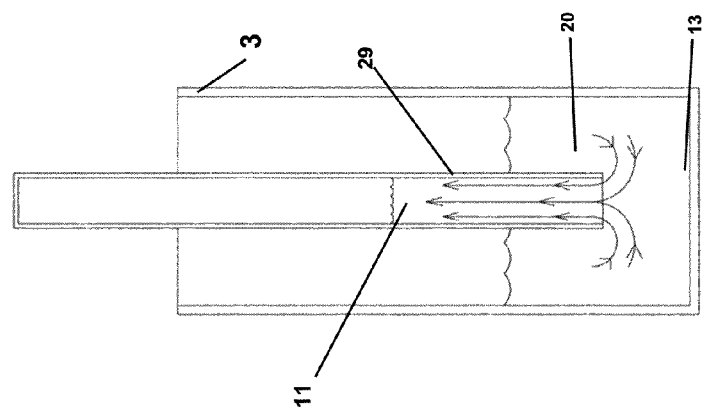
FIG. 4 shows an example of a probe aspirating a mixed component of an automated sample processing system in accordance with various embodiments of the present invention.

To obtain adequate mixing of the at least two components or mixed components, the present invention provides, in embodiments, an additional mixing step. An automatic vertical forced fluidic turbulent component mixer (25) may provide automatic vertically forced fluidic turbulent mixing of at least two mixing components in a mixing vial. In embodiments, this additional high-speed mixing step may provide an additional dip and mix step which at first glance may seem inefficient; however it may provide optimal mixing of the mixed components. As shown in FIGS. 4 and 5, a mixing component suction element (29) may be placed in a mixing vial (3) and into the liquid of the at least two components. A portion (11) of the mixed component may be aspirated from a mixing vial such as with perhaps a mixed component aspirator. A mixing component suction element (29) may be a mixed component aspirator. In embodiments, a portion (11) of the mixed component may include but is not limited to about 2 milliliters, about 1 millimeter, about 3 milliliter, about 20% of the total liquid of the at least two components in the mixing vial, about 30% of the total liquid of the at least two components in the mixing vial, about 33% of the total liquid of the at least two components in the mixing vial, about 35% of the total liquid of the at least two components in the mixing vial, about 40% of the total liquid of the at least two components in the mixing vial, about 50% of the total liquid of the at least two components in the mixing vial, and the like. Of course, any amount or percentage may be used including any percentage between 0 to 100%.

After aspiration, a mixing component suction element may move out of the liquid and perhaps even above a surface (16) of the component liquid. An automatic vertical forced fluidic turbulent component mixer (25) as shown in FIG. 5 may apply a vertical force (10) to the aspirated portion of mixed components creating a dispense portion (12) of mixed components to perhaps forcefully dispense the dispense portion of liquid back into a remaining pool (15) of mixed components in the mixing vial. The forceful dispense of liquid may be achieved with a component dispenser. The component mixer may be positioned in an upright direction perhaps even above a surface (16) of the remaining pool of liquid. In embodiments, a component mixer may apply vertical downward force to a dispense portion and perhaps even the remaining pool of liquid. In other embodiments, a component mixer may apply external force to the remaining pool of liquid. External may include force originating from outside the remaining pool of liquid. By forcefully dispensing the aspirated liquid of the combined components back into the remaining pool of liquid in the mixing vial, the components may create a forced mix movement (62) such as understood in FIG. 5. This may create a uniform suspension (4) of the at least two components and can provide better staining of the biological samples arranged on the slides.

In embodiments, a portion of mixed components may be dispensed at a dispense speed which may be about 100 steps per second, about 50 steps per second, about 200 steps per second, between about 50 steps per second and about 200 steps per second, between about 50 steps per second and about 400 steps per second, and the like. A step per second may relate motor steps in the case of a pump embodiment. A step in the X. or Y direction may be about 0.03 mm and a step in the Z direction may be about 0.0025 mm. In embodiments, a full speed range of a pump may be 10-2500 motor steps in standard resolution. The speed may not be limited but can be adjusted if necessary throughout the range.

The mixing step may be repeated until adequate uniform suspension is created. This may include but it is not limited to repeating up to two times, repeating up to three times, repeating up to four times, repeating up to five times or more, and the like. Thereafter, a uniform suspension may be automatically applied to a biological sample on the slide with perhaps an automatic uniform suspension slide applicator. In embodiments, an automatic uniform suspension slide applicator may be a probe (8) as shown in FIG. 3. Of course, in embodiments the present invention may provide multiple probes or alternatively may provide a single probe of which in between different aspiration and dispensing steps, there may be at least one washing step to prevent contamination of the system. For example, embodiments may provide a single probe (8) or may provide multiple probes (8) which may alone or in combination be a mixing component suction moment, an automatic uniform suspension slide applicator, a component transfer dispenser, a component dispenser, an automatic vertical force fluidic turbulent component mixer, an automatic downward vertical force fluidic turbulent component mixer, an external automatic vertical force fluidic turbulent component mixer, a repetitive automatic vertical force fluidic turbine component mixer, and the like. An automatic uniform suspension slide applicator may dispense a uniform suspension onto multiple slides at once including but not limited to up to about 10 slides or more.

In embodiments, a diluent or buffer of higher volume may be first added to a mixing vial then the rest of the components with lower volume may be added thereafter. If the chromogen or enzyme components are of little volume perhaps less than 500 µL they may be mixed in suspension and touch dispense may be implemented so that all the little volume is added to the buffer or diluent. A non-limiting example of a mixing formula may include: washing of a probe; aspirating a volume of greater than about 4500 (volumes splits) where perhaps volume may be aspirated and dispensed from about −20,000 (absolute position from home); a probe homes; aspirating a volume of less than about 4500, when a volume is less than or equal to about 500, liquid may be aspirated and dispensed from a Z depth of mixing vial plus about 2500 (touch dispense), when a volume is greater than about 500 and less than about 4500, it may be aspirated and dispensed from a reagent dispensed depth for mixing value; a probe homes, and the like. A non-limiting example of a mixing process in a mixing vial may include but is not limited to: a probe going down to Z depth for mixing vials; if the mix volume is greater than about 2 mL, then aspirate about 2 mL or else aspirate a calculated mix volume; probe moves up about 80,000 steps (in this step probe may be moved higher in the vial, for example if the vial is about 5 cm tall, the probe may dispense at 4 cm away from the bottom and may also dispense inside the vial to avoid splashing outside and may dispense at a higher speed about 100 which may be about 2 to 4 times greater in a component dispense to create a turbulence mixing of liquid in uniform mixing of two components); dispense reagents; probe homes; and perhaps even probe was washed. In a non-limiting example, component volumes of greater than about 1000 (up to about 4500 microliters) from reagent vials and/or cold spot vials may be aspirated at speed about 200; component volumes of less than or equal to about 1000 from reagent vials and/or cold spot vials may be aspirated at speed about 400; components may be dispensed into mixing vials at speed about 100. For actual mixing, a component in the mixing vials may be aspirated at speed about 100 and dispensed into the mixing vials at speed about 100.

In embodiments, a mixing system may allow a formula of reagents to be entered in the reagent manager (perhaps the user software interface for the instrument). In addition, the sequence of order of components to be mixed, the volume in microliters, the incubation time, stability of components, and perhaps even the end mixture may be entered in the reagent manager database. A stainer system perhaps in response to a software program may mix the components as per the formula ratio and may apply the reagent onto the slides. Based on the reconstituted stability at the end mixture, the scheduler may group slides during the staining run. The mixing formula can have any number of components in the total volume of the resultant mixture may be equal or less than 6 mL. If one of the components in a mix formula is unstable, software may request the user to load the component reagent in the cold spot in the cold spot will turn on automatically. With the components and formula in the software database, user can determine whether they would prefer to mix online or off-line. If an unstable reagent is mixed off-line, the software or hold the slides in buffer and may alert the user when to load the end of reagent mixture in the stainer to be used. For example, if a slide has a protocol with eight steps not including wash in between, the protocol can have to chromogen steps with one chromogen and its components stable mixed online in the next chromogen and one of its components unstable mixed online. Any mixing formula can be chosen to mix online or off-line. Software may automatically calculate the component mixer breakdown and may determine total mixed volume needed for slides. Components stored in the cold spot may be mixed before aspiration to assure uniform mixing in the vial and to avoid settling in sediment. If a chromogen is not a mixed type and is unstable, it may be placed in the cold spot, and may be directly dispensed on the slide.

Figure 6:
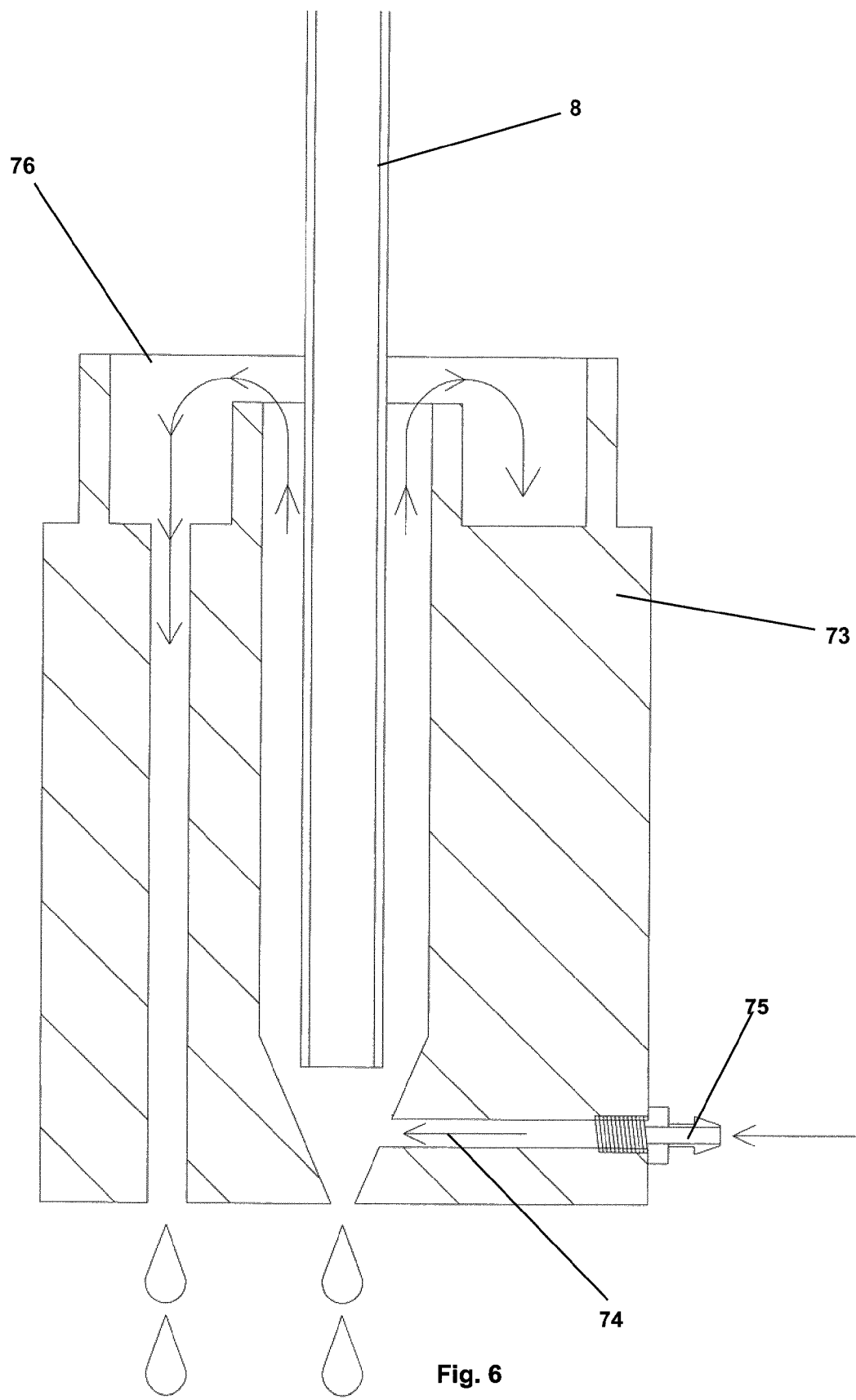
FIG. 6 shows an example of a washing probe of an automated sample processing system in accordance with various embodiments of the present invention.

As mentioned above, a probe (8) may be washed as shown in FIG. 6. In embodiments, a probe (8) may move into the center tube of the wash station (73). Clean wash solution (74), which may be a buffer, deionized water or the like, may be pumped into the center tube through a fitting (75) perhaps at a rate fast enough to rise up to the top and overflow into the drain portion (76) of the wash station. A small hole may allow a residual wash station to drain.

As shown in FIGS. 8 through 12, embodiments of the present invention may include an automatic dynamic component level detector (32) for perhaps the automatic dynamic detecting of component levels in an automated sample processing system and may even include an automatic improper apparatus assembly detector (33) for perhaps the automatic detecting improper assembly of an automated sample processing system. These detectors may provide the ability to detect component levels in a container, vial, mixing vials or the like, and perhaps even to detect improper assembly and the like to perhaps prevent system delays. Component level detection may include but is not limited to detection or detectors of component liquid levels, component use, remaining component levels, z-axis range of motion, and the like. Examples of an improper assembly may include but are not limited to missing parts, improperly installed parts, missing vials, vial caps left on, and the like. An automatic dynamic component level detector (32) and an automatic improper apparatus assembly detector (33) may provide detection with an ultrasound sensor.

Figure 10:
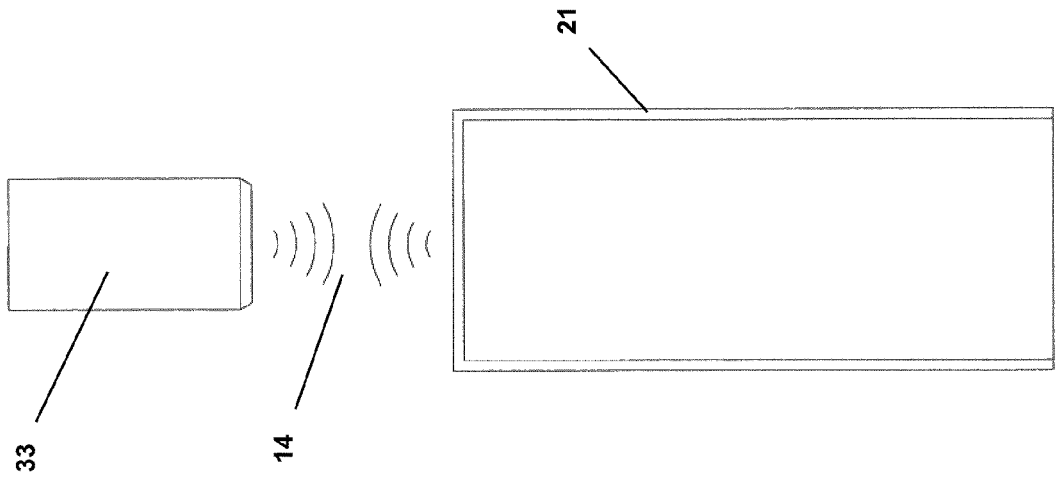
FIG. 10 shows an example of an automatic improper apparatus assembly detector detecting an upside down vial in accordance with various embodiments of the present invention.
Figure 9:
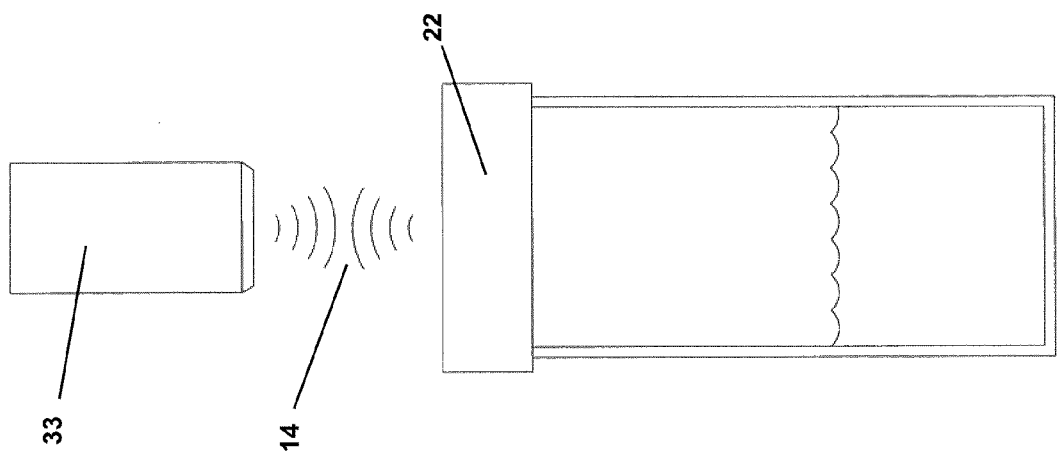
FIG. 9 shows an example of an automatic improper apparatus assembly detector detecting a cap in accordance with various embodiments of the present invention.
Figure 8:
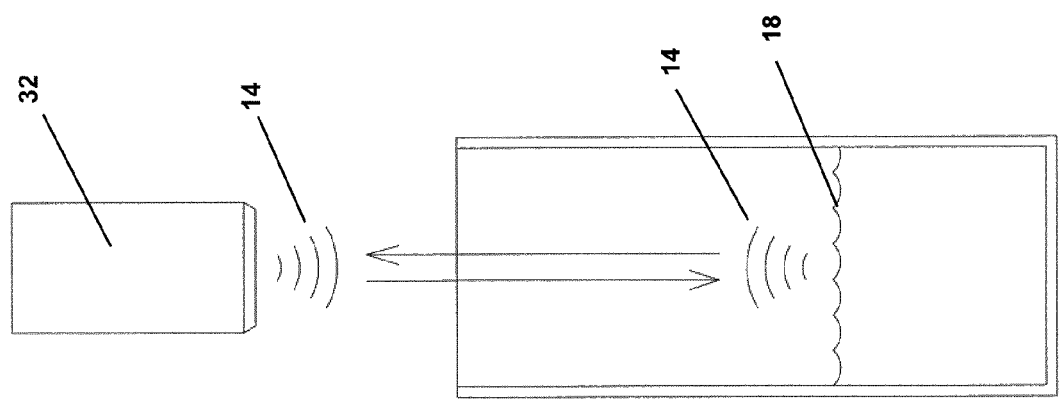
FIG. 8 shows an example of an automatic dynamic component level detector detecting a component liquid level in accordance with various embodiments of the present invention.

As shown in FIG. 8, an automatic dynamic component level detector (32) may use ultrasound waves (14) to detect a component level (18) of liquid in a vial. FIGS. 9 and 10 show an automatic improper apparatus assembly detector (33) using ultrasound waves (14) to detect a cap (22) and an upside down vial (21). FIGS. 11 and 12 show detectors using ultrasound waves (14) to detect liquid levels in a reagent vial (19) or perhaps to detect a cap (23) on a reagent vial. When conducting a sample process, response time may be short and a detector may allow for a quick scan of all of the positions in a very short period of time. Level sensing may be preformed by using sound waves and may not require a dispensing probe to touch a reagent for detection. Liquid levels may be determined prior to starting a staining run thereby making sure that an adequate amount is available for the run. Reagent levels may be used to determine the distance between the probe and the liquid. This information may be used to dip the probe just enough to aspirate the required amount of liquid perhaps thereby eliminating excess pickup and perhaps even maximizing reagent use. Level sensing information may be used in detecting reagent run out and perhaps eventual negative staining. Negative staining may be prevented by displaying appropriate notification to a user and perhaps even affected slides may be kept in buffer until an operator loads an adequate amount. Level sensing may also be used to Register reagents into the system. Registration may be a process of adding reagents to the system inventory. Of course, other detection methods may be used.

Additional features of an automatic dynamic component level detector (32) may include but are not limited to the following: no contact with reagents for fast initial reagent volumes scan; alerts user if there is insufficient volume of reagent to complete the program staining run; probe does not require washing between level detection of different reagents, reducing the overall runtime; level Sensor detects missing or improperly installed mixing vials; alerts user if mixing vials are missing or installed upside down; alerts user if there are not enough mixing vials to complete the program staining run; level sensor detects if caps been left on the reagent vials, preventing robot crashes; and perhaps even level sensor calibrates vial height for proper calibration of the Z-axis range of motion; automatic calibration of Z-axis range of motion ensures minimum residual dead volume and may prevent probe contact with the bottom of the reagent vial; and the like.

In embodiments of the present invention may provide combining an automatic dynamic component level detector with a capacitance detector. One benefit of using an automatic dynamic detector perhaps even an ultrasound sensor may be that the sensor does not touch the reagent to detect liquid levels and therefore may decrease contamination and additional washing steps thereof. Another benefit of combining an ultrasound and capacitance sensor may be real-time correction of the initial level reading from the ultrasound sensor and perhaps even the minimizing of dead volume left in the vials. The inclusion of an additional capacitance or inductive sensor may be built into a reagent dispensing probe. A probe may detect the level of reagents when it contacts the surface of the liquid. When used in combination with the ultrasonic sensor, the run may not be delayed since the probe may be making a secondary level reading perhaps at a point in the run where the probe may require washing. The level sensing by a probe may adjust the initial ultrasonic reading for highly accurate level readings.

An example of the sequence of events for an initial reagent volumes scan may include but are not limited to: a robot may move the ultrasonic sensor located in Z-head to a calibrated position over the first reagent vial position in the reagent rack; a robot may move the ultrasonic sensor in the Y-axis sequentially to each reagent position; an ultrasonic sensor may pause briefly over the position associated with the opening of the reagent vial and may emit sound waves which reflect off the surface of the liquid in the vial; the reflection may be captured by the ultrasonic sensor; the time it takes the reflection to return to the sensor may be used to calculate the liquid level in each vial; if the calculated reagent volume is not enough to perform all of the operations required by the previously programmed protocols, the stainer program will alert the user to which reagents are low or perhaps missing and how much additional reagent(s) may Be required to complete the staining run.

An example of the sequence of events for detection of mixing vials may include but are not limited to: a robot may move the ultrasonic sensor located in the Z-head to a calibrated position over the first mixing vial position in the mixing vial rack; a robot may move the ultrasonic sensor in the Y-axis sequentially to each mixing vial position; an ultrasonic sensor may pause briefly over the position associated with the opening of the mixing vial and may emit sound waves which reflect off the bottom of the vial; the reflection may be captured by the ultrasonic sensor; the time it takes the reflection to return to the sensor may be used to calculate and compare the readings to the known distance to the bottom of the mixing vials; if the distance is greater than the known distance of the vial bottom, the vial may be missing and the user may be alerted to this condition for correction; if the distance is less than the known distance of the vial bottom, the vial either is installed upside down or may contain residual reagents from a previous run; the user may be alerted to these conditions for correction; and perhaps even the instrument may re-scan the rack to confirm the corrections have been made before proceeding with the staining run; and the like.

An example of the sequence of events for cap detection may include but are not limited to: a robot may move an ultrasonic sensor located on the Z-head to a calibrated position over the first reagent vial position in the reagent rack; a robot may move the ultrasonic sensor in the Y-axis sequentially to each reagent position; the ultrasonic sensor may pause briefly over the position associated with the opening of the reagent vial and may emit sound waves which reflect off the surface of the liquid in the vial; the reflection may be captured by the ultrasonic sensor; the time it takes the reflection to return to the sensor may be used to calculate the liquid level and each vial; if the reading indicates a distance too close to the sensor, the vial may have the cap installed; and perhaps even the user may be alerted to remove the cap to prevent collision with the reagent probe; the instrument may rescan the rack to confirm the corrections have been made before proceeding with the staining run; and the like.

An example of the sequence of events for calibration of reagent vial height may include but are not limited to: a robot may move the ultrasonic sensor located in the Z-head to a calibrated position over the first reagent vial position in the reagent rack; a robot may move the ultrasonic sensor and the Y-axis sequentially to each reagent position; the ultrasonic sensor may pause briefly over the position associated with the identification label of the reagent vial and may emit sound waves which reflect off the surface of the vial; the reflection may be captured by the ultrasonic sensor; the time it takes the reflection to return to the sensor may be used to calculate the height that each vial is sitting in the reagent rack; the height of each vial may be used to adjust the maximum Z-axis motion of the reagent probe; and perhaps even this may prevent the probe crashing into the vial bottom and may minimize residual reagents in the vial; and the like.

An example of the sequence of events for a combination of ultrasonic and probe sensors may include but are not limited to: a robot may move the ultrasonic sensor located on the Z-head to a calibrated position over the first reagent vial position in the reagent rack; a robot may move the ultrasonic sensor in the Y-axis sequentially to each reagent position; the ultrasonic sensor may pause briefly over the position associated with the opening of the reagent vial and may emit sound waves which reflect off the surface of the liquid in the vial; the reflection may be captured by the ultrasonic sensor; the time it takes the reflection to return to the sensor may be used to calculate the liquid level in each vial; if the calculated reagent volume is not enough to perform all of the operations required by the previously programmed protocols, the stainer program may alert the user to which reagents are low or missing and how much additional reagent(s) may be required to complete the staining run; during the course of the staining run the probe may move into each reagent vial to aspirate reagent and dispense on the slides; as the probe enters the reagent vial and makes contact with the surface of the liquid, a change in capacitance (or in any other embodiment, such as inductance) between the probe and a metal plate installed underneath the reagent vials by an electronic circuit in the stainer; the amount of change in capacitance may be proportional to the liquid level in the vial; since the probe sensor may actually touch the reagent, a more accurate level can be detected; and perhaps even this reading can be used to adjust the initial reading throughout the staining run to alert the user of any abnormal use of reagents; and the like.

As shown in FIG. 13, an automated sample processing system (34) may provide a process operation control system. In embodiments, a process operation control system may include a computer system which may provide an inventory management interface to perhaps track the reagent lot number, expiration dates and remaining reagent volume, providing easy access for reporting or reagent tracking giving confidence that expired reagents will not be used. Software may be provided with the capability to control up to 4 instruments or more from one computer; enabling data-sharing of protocols, reagent inventory, test and patient information. Software may also feature the capacity to generate multiple reports. These reports include protocol validation, IHC summary by a batch/run and reagent usage. This feature may enable easy sample tracking and essential documentation for laboratory requirements.

In embodiments, methods of automated recovery sample processing may include establishing an automated sample processing system configured to at least partially process of biological sample arranged on the slide, initiating an automatic sample processing run to at least partially process said biological sample arranged on said slide in response to such automated sample processing system, fortuitously terminating an automatic sample processing run, restarting such automated sample processing system after said fortuitous termination, automatically detecting at least one immediate condition of said fortuitously terminated automatic sample processing run, automatically calculating a reconstructed automatic sample processing run based on said at least one immediate condition of said fortuitously terminated automatic sample processing run, and perhaps even initiating a reconstructed automatic sample processing run to complete said at least partially process said biological sample arranged on said slide. A recovery system for automated sample processing may include an automated sample processing system, at least one biological sample arranged on at least one slide, an automatic sample processing run initiator, an automatic fortuitous sample processing run termination detector, and automatic terminated sample processing run immediate condition determinator responsive to set automatic fortuitous ample processing run termination detector, and automatic terminated sample processing run reconstruction calculator responsive to set automatic terminated sample processing run immediate condition determinator, and perhaps even a reconstructed automatic sample processing run initiator responsive to said terminated sample processing run reconstruction calculator.

As shown in FIG. 13, an automated sample processing system (34) may process at least one biological sample arranged on at least one slide. A system run may begin by initiating an automatic sample processing run with perhaps an automatic sample processing run initiator (35). In embodiments, a system run may be an automatic sample staining run of the biological samples arranged on slides with perhaps an automatic sample stain initiator. The initiation may include a user input to begin the run. In the event the automatic sample processing run is fortuitously terminated by perhaps a termination event, an automatic fortuitous sample processing run termination detector (36) may detect such termination. A termination event may include but is not limited to an inadvertent software termination, a computer crash, a temporary power blackout, emergency operator termination, and the like. An automated sample processing system may be restarted (37) after the fortuitous termination. As a non-limiting example, an automated sample processing system may be restarted by powering on the system. A recovery sample processing system may not always require powering on the processing system. One example scenario could be a forced application termination by the operator without powering down the system. Recovery however may require restarting the processing system. In embodiments, the present invention may provide automatic detection of an incomplete run with perhaps an automatic incomplete run detector (41).

After the system has restarted, it may detect that the system was terminated prior to completion perhaps by chance or unintentionally or even accidentally. After restarting the system, it may automatically detect at least one immediate condition of the sample processing run perhaps with an automatic terminated sample processing run immediate condition determinator (38). The system may be program to automatically check various parts of the system to gather information on the status of the run for later processing. For example an immediate condition may include but is not limited to: immediate slide information, immediate component information, an amount of stain, an amount of remaining component, or the like information. An immediate condition may include those conditions that immediately apply to the system when it is restarted. Once enough information may be assembled, a system may automatically calculate a reconstructed automatic sample processing run based on at least one immediate condition of the fortuitously terminated automatic sample processing run with perhaps an automatic terminated sample processing run reconstruction calculator (39). The calculation may automatically determine a new run starting point so as to perhaps salvage the previously terminated run. In embodiments, the system may provide a user slide deselection or perhaps even user slide selection option (40) prior to proceeding the reconstructed automatic sample processing run. This may allow a user to provide additional input on how to proceed with the reconstructed run for example by selecting or deselecting specific slides for processing. In some conditions, user slide selection option may be provided instead of deselection or vice versa. One example may be where a slide has over incubated at the time of run reconstruction and it may not provide a reliable result if processed. User may be provided with an option to select the slide. A system may initiate a reconstructed automatic sample processing run to complete at least partially processing a biological sample arranged on a slide with perhaps a reconstructed automatic sample processing run initiator (42). The initiating step may be a one click initiating step perhaps with a one click reconstructed automatic sample processing run initiator (43) such as shown in FIG. 14 where an example of a one click computer screen option, "Recover", is presented.

The embodiments relating to a reconstructed system due to such fortuitous termination may be very different from a system which integrates stats slides. In the present invention, the terminated system they have to rebuild the database, detect the present conditions, and the like which is unlike reconfiguring with stat slides.

In embodiments, the present invention may provide methods and systems of efficient slide cleaning and automated sample processing. Methods may include establishing an automated sample processing system configured to at least partially process at least one biological sample arranged at least one slide and perhaps even single sweep applying a multi-treatment cleaning cycle to an upper surface of said at least one slide. Systems may include an automated sample processing system configured to at least partially process at least one biological sample arranged on at least one slide, a single sweep multi-treatment cleaning applicator responsive to sit automated sample processing system, and perhaps even a liquid wash source connected to said single sweep multi-treatment cleaning applicator.

As shown in FIG. 7, a multi-treatment cleaning cycle (46) may be provided, in embodiments, to clean at least one slide before, during, or even after the sample process with perhaps a single sweep multi-treatment cleaning applicator (51). A multi-treatment cleaning cycle applicator may be applied to an upper surface (45) of at least one slide in a single sweep. The multi-treatment cleaning may include a washing treatment with perhaps a wash applicator (44) and a drying treatment with perhaps a dry applicator (47) during the single sweep application. In embodiments, a liquid wash source (58) may be connected (either directly or indirectly) and perhaps even an air compressor (60) or any type of air source may be connected (either directly or indirectly) to a single sweep multi-treatment cleaning applicator (51). The washing treatment may provide washing of an upper surface of a slide with a buffer (48) and the drying treatment may provide drying of the upper surface of the slide with forced air (49). A buffer may include any type of slide washing buffer including but not limited to: DAB substrate buffer, Vulcan Buffer, medical heat-induced epitope retrieval buffer, decloaking solutions buffer, and the like. A multi-treatment cleaning cycle may be applied with a multi-treatment cleaning cycle applicator from above the upper surface of the slide. In embodiments, a slide may be located in a substantially horizontal position or perhaps a slide may be located at an angled position to perhaps provide angling of the slide. In other embodiments, a single sweep multi-treatment cleaning applicator may be placed perpendicular to the slide or may even be positioned off-axis to the slide. Off axis positioning may include any position off of a central bisecting line. Therefore, many different applicator and slide positions are available for optimal cleaning and may be dependent on how the system is set up including but not limited to where the applicators are located, where the drainage is located, where liquid sources are located, and the like.

A single sweep multi-treatment cleaning applicator may provide a single movement (50) across at least one slide perhaps by moving an applicator from one end (52) of the slide to an opposite end (53) of the slide. A single movement of the single sweep multi-treatment cleaning applicator may simultaneously dispense wash fluid with blowing air to the upper surface of the slide. A wash treatment (44) may include a wash fluid dispenser and a drying treatment (47) may include an air dispenser is understood from FIG. 7. A wash fluid dispenser may be located in front of an air dispenser and may even provide dispensing wash fluid parallel to air. Specifically, in embodiments, a single sweep application may include pushing an existing slide reagent (55) on a slide with a buffer (48) dispensed in a washing treatment (44) and pushing the dispensed buffer (56) on the slide with air (49) dispensed in a drying treatment (47) therefore perhaps providing a reagent pushing applicator and a wash pushing applicator. In embodiments, a wash fluid dispenser may dispense an amount of fluid between about 6 milliliters to about 7 milliliters of wash fluid on a slide. Of course, any amount of fluid maybe dispensed and all amounts are meant to be included in this application. The system may terminate the dispensing of the wash fluid for a least part of the single sweep application step with perhaps a wash fluid dispense terminator. In embodiments, termination of the wash fluid may occur about halfway (57) through the single sweep applying step. Embodiments of the single sweep multi-treatment cleaning may be important from an efficiency perspective and may provide enhanced cleaning of the slide. If more than one wash is required, the single sweep multi-treatment cleaning step may be repeated.

In embodiments, the present invention may provide applying a quenching buffer to the slide after the step of single sweep applying said multi-treatment cleaning cycle. A quenching buffer may be applied from the liquid wash source (58) by the washing treatment (44) of the cleaning applicator. In embodiments, an amount of quenching buffer applied to a slide may be between about 3 milliliters to about 4 milliliters of quenching buffer. Of course, any amount of quenching buffer may be used and all amounts are meant to be included in this application. In other embodiments, the multi-treatment cleaning cycle applicator may be responsive to a robotic motion system as described herein.

As can be easily understood from the foregoing, the basic concepts of the present invention may be embodied in a variety of ways. It involves both automated sample processing techniques as well as devices to accomplish the appropriate automated sample processor. In this application, the automated sample processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "mixer" should be understood to encompass disclosure of the act of "mixing"—whether explicitly discussed or not—and, conversely, were there effectively disclosure of the act of "mixing", such a disclosure should be understood to encompass disclosure of a "mixer" and even a "means for us mixing." Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the Information Disclosure Statement or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the automated sample processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 715 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of combining reagent in an automated sample processing system comprising the steps of:
    dispensing a liquid biological sample processing substance into a mixing vial with at least one probe of an automated sample processing system;
    dispensing at least one additional biological sample processing substance into said mixing vial containing said liquid biological sample processing substance with said at least one probe of said automated sample processing system to create a mixture of at least two biological sample processing substances in said mixing vial;
    contacting at least part of said at least one probe with said mixture of said at least two biological sample processing substances in said mixing vial;
    aspirating at least a portion of said mixture of said at least two biological sample processing substances from said mixing vial with said at least one probe contacted with said mixture;
    forcefully dispensing said aspirated portion of said mixture of at least two biological sample processing substances back into said mixing vial with said at least one probe so as to provide automatic vertically forced fluidic turbulent mixing of said mixture of at least two biological sample processing substances in said mixing vial to create a uniform suspension of said mixture of at least two biological sample processing substances; and
    automatically applying at least a portion of said uniform suspension to a biological sample on a slide with said at least one probe.

2. The method of combining reagent in an automated sample processing system according to claim 1 wherein said steps of dispensing said biological sample processing substances into said mixing vial and dispensing said aspirated portion of said mixture back into said mixing vial comprises the step of providing a robotic arm connected to said at least one probe of said automated sample processing system.

3. The method of combining reagent in an automated sample processing system according to claim 1 and further comprising the step of providing at least one biological sample processing substance source in said automated sample processing system.

4. The method of combining reagent in an automated sample processing system according to claim 3 and further comprising the steps of:
   suctioning at least one biological sample processing substance from said at least one biological sample processing substance source with said at least one probe.

5. The method of combining reagent in an automated sample processing system according to claim 1 wherein said automated sample processing system comprises an automated immunohistochemistry sample processing system.

6. The method of combining reagent in an automated sample processing system according to claim 1 wherein said mixture of at least two biological sample processing substances comprises a mixture selected from a group consisting of at least three biological sample processing substances, at least four biological sample processing substances, at least five biological sample processing substances, at least six biological sample processing substances, at least seven biological sample processing substances, at least eight biological sample processing substances, at least nine components, and at least ten biological sample processing substances.

7. The method of combining reagent in an automated sample processing system according to claim 1 wherein said mixture of at least two biological sample processing substances comprises up to eight biological sample processing substances.

8. The method of combining reagent in an automated sample processing system according to claim 1 wherein said biological sample processing substance is selected from a group consisting of at least one reagent, at least one chromogen, at least one chemical, at least one enzyme, and any combination thereof.

9. The method of combining reagent in an automated sample processing system according to claim 1 wherein said step of dispensing said aspirated portion of said mixture into said mixing vial with said at least one probe so as to provide automatic vertically forced fluidic turbulent mixing of said at least two biological sample processing substances comprises the step of dispensing said aspirated portion of said mixture into said mixing vial with said at least one probe so as to provide automatic vertical downward forced fluidic turbulent mixing of said at least two biological sample processing substances.

10. The method of combining reagent in an automated sample processing system according to claim 1 wherein said step of dispensing said aspirated portion of said mixture into said mixing vial with said at least one probe so as to provide automatic vertically forced fluidic turbulent mixing of said at least two biological sample processing substances comprises the step of dispensing said aspirated portion of said mixture into said mixing vial with said at least one probe so as to provide external automatic vertically forced fluidic turbulent mixing of said at least two biological sample processing substances.

11. The method of combining reagent in an automated sample processing system according to claim 1 wherein said step of dispensing said aspirated portion of said mixture into said mixing vial with said at least one probe comprises the step of dispensing said aspirated portion of said mixture into said mixing vial with said at least one probe located above a surface of a remaining pool of said mixture left in said mixing vial after said aspirating step.

12. The method of combining reagent in an automated sample processing system according to claim 11 wherein said step of dispensing said aspirated portion of said mixture into said remaining pool of said mixture comprises the step of forcefully dispensing said aspirated portion of said mixture into said remaining pool at a speed between about 50 steps per second and about 400 steps per second.

13. The method of combining reagent in an automated sample processing system according to claim 11 and further comprising the step of repeating said steps of aspirating at least said portion of said mixture and dispensing said aspirated portion of said mixture into said remaining pool of said mixture.

14. The method of combining reagent in an automated sample processing system according to claim 1 wherein said step of dispensing said aspirated portion of said mixture into said mixing vial comprises the step of dispensing said aspirated portion of said mixture into said mixing vial between about 50 steps per second and about 400 steps per second.

15. The method of combining reagent in an automated sample processing system according to claim 1 wherein said step of automatically applying at least said portion of said uniform suspension with said at least one probe comprises the step of applying said uniform suspension to up to about 50 biological samples with said at least one probe.

16. The method of combining reagent in an automated sample processing system according to claim 1 wherein said step of dispensing said at least one additional biological sample processing substance into said mixing vial with said at least one probe comprises the step of dispensing said at least one additional biological sample processing substance at a base of said mixing vial with said at least one probe.

17. The method of combining reagent in an automated sample processing system according to claim 1 and further comprising the step of providing a maximum liquid volume in said mixing vial of up to about 6 milliliters after said at least one additional biological sample processing substance has been dispensed into said mixing vial with said at least one probe.

18. The method of combining reagent in an automated sample processing system according to claim 1 and further comprising the step of repeating said steps of aspirating at least said portion of said mixture and dispensing said aspirated portion of said mixture.

19. The method of combining reagent in an automated sample processing system according to claim 18 or 13 wherein said step of repeating is selected from a group consisting of repeating up to two times, repeating up to three times, repeating up to four times, and repeating up to five times.

20. The method of combining reagent in an automated sample processing system according to claim 1 wherein said aspirated portion of said mixture comprises an amount of aspirated mixture selected from a group consisting of about 2 milliliters, about 1 milliliter, about 3 milliliter, about 20% of said at least two components in said mixing vial, about 30% of said at least two components in said mixing vial, about 33% of said at least two components in said mixing vial, about 35% of said at least two components in said mixing vial, about 40% of said at least two components in said mixing vial, and about 50% of said at least two components in said mixing vial.

21. The method of combining reagent in an automated sample processing system according to claim 1 and further comprising the step of storing said biological sample processing substances in a cold station of said automated sample processing system.

22. The method of combining reagent in an automated sample processing system according to claim 1 and further comprising the step of automatic dynamic detecting a liquid level with a detector of said automated sample processing system.

23. The method of combining reagent in an automated sample processing system according to claim 22 wherein said detector comprises an ultrasound sensor.

24. The method of combining reagent in an automated sample processing system according to claim 23 wherein said detector comprises a capacitance detector.

25. The method of combining reagent in an automated sample processing system according to claim 22 wherein said step of automatic dynamic detecting said liquid level with said detector comprises a step selected from a group consisting of detecting biological sample processing substance use, detecting remaining liquid levels, and detecting with a z-axis range of motion of a detector.

26. The method of combining reagent in an automated sample processing system according to claim 1 further comprising the step of automatic detecting an improper assembly of said automated sample processing system.

27. The method of combining reagent in an automated sample processing system according to claim 26 wherein said step of automatic detecting said improper assembly comprises the step of automatic detecting said improper assembly with an ultrasound sensor.

28. The method of combining reagent in an automated sample processing system according to claim 26 wherein said step of detecting said improper assembly comprises a step selected from a group consisting of detecting missing parts in said automated sample processing system, detecting improperly installed parts in said automated sample processing system, detecting missing vials in said automated sample processing system, and detecting a presence of a vial cap in said automated sample processing system.

29. The method of combining reagent in an automated sample processing system according to claim 1 wherein said biological sample processing substance is selected from a group consisting of at least one ancillary titration component and at least one antibody titration component.

30. The method of combining reagent in an automated sample processing system according to claim 1 wherein said biological sample processing substance comprises at least one antibody diluent.

31. The method of combining reagent in an automated sample processing system according to claim 1 wherein said biological sample processing substance comprises at least one buffer.

* * * * *